United States Patent
Chalekian et al.

(10) Patent No.: US 10,398,550 B2
(45) Date of Patent: Sep. 3, 2019

(54) ATRAUMATIC INTERFACE IN AN IMPLANT DELIVERY DEVICE

(71) Applicant: St. Jude Medical, Cardiology Division, Inc., St. Paul, MN (US)

(72) Inventors: Aaron J. Chalekian, Savage, MN (US); Ralph J. Thomas, Champlin, MN (US); Gary W. Geiger, Fridley, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 528 days.

(21) Appl. No.: 15/021,170

(22) PCT Filed: Sep. 10, 2014

(86) PCT No.: PCT/US2014/054950
§ 371 (c)(1),
(2) Date: Mar. 10, 2016

(87) PCT Pub. No.: WO2015/038615
PCT Pub. Date: Mar. 19, 2015

(65) Prior Publication Data
US 2016/0220369 A1 Aug. 4, 2016

Related U.S. Application Data

(60) Provisional application No. 61/877,104, filed on Sep. 12, 2013.

(51) Int. Cl.
*A61F 2/24* (2006.01)
*A61F 2/962* (2013.01)
*A61F 2/966* (2013.01)

(52) U.S. Cl.
CPC .......... *A61F 2/2436* (2013.01); *A61F 2/962* (2013.01); *A61F 2/966* (2013.01)

(58) Field of Classification Search
CPC .......... A61F 2/2436; A61F 2/95; A61F 2/962; A61F 2/966; A61F 2002/011; A61F 2002/9517; A61F 2002/9534
See application file for complete search history.

(56) References Cited

U.S. PATENT DOCUMENTS 3,657,744 A 4/1972 Ersek
4,423,730 A 1/1984 Gabbay
(Continued)

FOREIGN PATENT DOCUMENTS

DE 102005003632 A1 8/2006
EP 1129744 A1 9/2001
(Continued)

OTHER PUBLICATIONS

International Search Report and Written Opinion for Application No. PCT/US2014/054950 dated Nov. 25, 2014.
(Continued)

*Primary Examiner* — Katrina M Stransky
*Assistant Examiner* — Lindsey Bachman
(74) *Attorney, Agent, or Firm* — Lerner, David, Littenberg, Krumholz & Mentlik, LLP

(57) ABSTRACT

A delivery device (10) for a collapsible prosthetic heart valve may include an operating handle (20, 220, 320) having a housing (30, 230, 330) and a carriage selectively (40) fixed or movable relative to the housing, and a catheter assembly (16, 116, 216, 416). The catheter assembly may have an inner shaft (26, 126, 226, 326, 426) around which a compartment (23) is defined, an outer shaft (22) surrounding at least a portion of the inner shaft, a distal sheath (24) fixedly connected to the outer shaft, and a mechanism configured to apply a distal force to the outer shaft while the carriage (40) is fixed relative to the housing (30, 230, 330) to stretch the outer shaft from a compressed length to an extended length. The extended length may be greater than the compressed length along an axis of elongation of the outer shaft (22).

20 Claims, 5 Drawing Sheets

(56) References Cited

U.S. PATENT DOCUMENTS

| | | |
|---|---|---|
| 4,471,777 A | 9/1984 | McCorkle, Jr. |
| 4,546,759 A | 10/1985 | Solar |
| 4,575,371 A | 3/1986 | Nordqvist et al. |
| 5,078,720 A | 1/1992 | Burton et al. |
| 5,090,958 A | 2/1992 | Sahota |
| 5,120,299 A | 6/1992 | Lombardi |
| 5,334,160 A | 8/1994 | Ellis |
| 5,411,552 A | 5/1995 | Andersen et al. |
| 5,415,664 A | 5/1995 | Pinchuk |
| 5,484,444 A | 1/1996 | Braunschweiler et al. |
| 5,534,007 A | 7/1996 | St. Germain et al. |
| 5,702,418 A | 12/1997 | Ravenscroft |
| 5,733,325 A | 3/1998 | Robinson et al. |
| 5,795,325 A | 8/1998 | Valley et al. |
| 5,797,952 A | 8/1998 | Klein |
| 5,824,041 A | 10/1998 | Lenker et al. |
| 5,827,324 A | 10/1998 | Cassell et al. |
| 5,843,167 A | 12/1998 | Dwyer et al. |
| 5,868,706 A | 2/1999 | Cox |
| 5,924,424 A | 7/1999 | Stevens et al. |
| 5,968,068 A | 10/1999 | Dehdashtian et al. |
| 5,980,533 A | 11/1999 | Holman |
| 6,077,297 A | 6/2000 | Robinson et al. |
| 6,190,357 B1 | 2/2001 | Ferrari et al. |
| 6,214,036 B1 | 4/2001 | Letendre et al. |
| 6,231,588 B1 | 5/2001 | Zadno-Azizi |
| 6,269,819 B1 | 8/2001 | Oz et al. |
| 6,306,141 B1 | 10/2001 | Jervis |
| 6,312,407 B1 | 11/2001 | Zadno-Azizi et al. |
| 6,361,545 B1 | 3/2002 | Macoviak et al. |
| 6,375,668 B1 | 4/2002 | Gifford et al. |
| 6,391,050 B1 | 5/2002 | Broome |
| 6,468,299 B2 | 10/2002 | Stack et al. |
| 6,482,228 B1 | 11/2002 | Norred |
| 6,607,551 B1 | 8/2003 | Sullivan et al. |
| 6,623,518 B2 | 9/2003 | Thompson et al. |
| 6,776,791 B1 | 8/2004 | Stallings et al. |
| 6,814,746 B2 | 11/2004 | Thompson et al. |
| 6,830,584 B1 | 12/2004 | Seguin |
| 7,018,406 B2 | 3/2006 | Seguin et al. |
| 7,311,730 B2 | 12/2007 | Gabbay |
| 7,510,572 B2 | 3/2009 | Gabbay |
| 7,682,390 B2 | 3/2010 | Seguin |
| 7,803,185 B2 | 9/2010 | Gabbay |
| 8,414,644 B2 | 4/2013 | Quadri et al. |
| 8,608,792 B2 | 12/2013 | Silveira et al. |
| 8,840,663 B2 | 9/2014 | Salahieh et al. |
| 2002/0120323 A1 | 8/2002 | Thompson et al. |
| 2003/0014007 A1 | 1/2003 | Eidenschink et al. |
| 2003/0023265 A1 | 1/2003 | Forber |
| 2003/0050694 A1 | 3/2003 | Yang et al. |
| 2003/0199963 A1 | 10/2003 | Tower et al. |
| 2004/0087900 A1 | 5/2004 | Thompson et al. |
| 2004/0093063 A1 | 5/2004 | Wright et al. |
| 2004/0204749 A1 | 10/2004 | Gunderson |
| 2004/0210304 A1 | 10/2004 | Seguin et al. |
| 2004/0236406 A1 | 11/2004 | Gregorich |
| 2004/0267346 A1 | 12/2004 | Shelso |
| 2004/0267348 A1 | 12/2004 | Gunderson et al. |
| 2005/0020974 A1 | 1/2005 | Noriega et al. |
| 2005/0027345 A1 | 2/2005 | Horan et al. |
| 2005/0033398 A1 | 2/2005 | Seguin |
| 2005/0049667 A1 | 3/2005 | Arbefeuille et al. |
| 2005/0049674 A1 | 3/2005 | Berra et al. |
| 2005/0065590 A1 | 3/2005 | Shelso |
| 2005/0137695 A1 | 6/2005 | Salahieh et al. |
| 2005/0137697 A1 | 6/2005 | Salahieh et al. |
| 2005/0222662 A1 | 10/2005 | Thompson et al. |
| 2006/0074484 A1 | 4/2006 | Huber |
| 2006/0100688 A1 | 5/2006 | Jordan et al. |
| 2006/0106415 A1 | 5/2006 | Gabbay |
| 2006/0111771 A1 | 5/2006 | Ton et al. |
| 2006/0142848 A1 | 6/2006 | Gabbay |
| 2006/0149294 A1 | 7/2006 | Argentine et al. |
| 2006/0167468 A1 | 7/2006 | Gabbay |
| 2006/0195184 A1 | 8/2006 | Lane et al. |
| 2006/0259120 A1 | 11/2006 | Vongphakdy et al. |
| 2006/0276872 A1 | 12/2006 | Arbefeuille et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0142858 A1 | 6/2007 | Bates |
| 2007/0162100 A1 | 7/2007 | Gabbay |
| 2007/0168013 A1 | 7/2007 | Douglas |
| 2007/0203561 A1 | 8/2007 | Forster et al. |
| 2007/0203575 A1 | 8/2007 | Forster et al. |
| 2007/0239271 A1 | 10/2007 | Nguyen |
| 2007/0244552 A1 | 10/2007 | Salahieh et al. |
| 2007/0292934 A1 | 12/2007 | Sorge |
| 2007/0293930 A1 | 12/2007 | Wang et al. |
| 2007/0293934 A1 | 12/2007 | Grewe |
| 2008/0071369 A1 | 3/2008 | Tuval et al. |
| 2008/0103443 A1 | 5/2008 | Kabrick et al. |
| 2008/0114443 A1 | 5/2008 | Mitchell et al. |
| 2008/0147182 A1 | 6/2008 | Righini et al. |
| 2008/0221666 A1 | 9/2008 | Licata et al. |
| 2008/0228255 A1 | 9/2008 | Rust et al. |
| 2008/0255662 A1 | 10/2008 | Stacchino et al. |
| 2008/0262590 A1 | 10/2008 | Murray |
| 2008/0319526 A1 | 12/2008 | Hill et al. |
| 2009/0036966 A1 | 2/2009 | O'Connor et al. |
| 2009/0054975 A1 | 2/2009 | del Nido et al. |
| 2009/0143851 A1 | 6/2009 | Paul, Jr. |
| 2009/0204197 A1 | 8/2009 | Dorn et al. |
| 2009/0222035 A1 | 9/2009 | Schneiderman |
| 2009/0228093 A1 | 9/2009 | Taylor et al. |
| 2009/0276027 A1 | 11/2009 | Glynn |
| 2009/0281610 A1 | 11/2009 | Parker |
| 2009/0287290 A1 | 11/2009 | Macaulay et al. |
| 2010/0004740 A1 | 1/2010 | Seguin et al. |
| 2010/0131039 A1 | 5/2010 | Chau et al. |
| 2010/0145438 A1 | 6/2010 | Barone |
| 2010/0152834 A1 | 6/2010 | Hannes et al. |
| 2010/0268315 A1 | 10/2010 | Glynn et al. |
| 2010/0286768 A1 | 11/2010 | Alkhatib |
| 2010/0298931 A1 | 11/2010 | Quadri et al. |
| 2010/0312325 A1 | 12/2010 | Dorn |
| 2011/0029065 A1 | 2/2011 | Wood et al. |
| 2011/0077731 A1 | 3/2011 | Lee et al. |
| 2011/0078350 A1 | 3/2011 | Carls |
| 2011/0098805 A1 | 4/2011 | Dwork et al. |
| 2011/0137401 A1 | 6/2011 | Dorn et al. |
| 2011/0172764 A1 | 7/2011 | Badhwar |
| 2011/0224678 A1 | 9/2011 | Gabbay |
| 2011/0251666 A1 | 10/2011 | Schmitt et al. |
| 2011/0251679 A1 | 10/2011 | Wiemeyer et al. |
| 2011/0257720 A1 | 10/2011 | Peterson et al. |
| 2011/0264201 A1 | 10/2011 | Yeung et al. |
| 2011/0264202 A1 | 10/2011 | Murray, III et al. |
| 2011/0288636 A1 | 11/2011 | Rolando et al. |
| 2011/0301685 A1 | 12/2011 | Kao |
| 2012/0078350 A1 | 3/2012 | Wang et al. |
| 2012/0123528 A1* | 5/2012 | Knippel ............... A61F 2/2436 623/2.11 |
| 2013/0131775 A1 | 5/2013 | Hadley et al. |
| 2013/0204344 A1 | 8/2013 | Tatalovich et al. |
| 2013/0274860 A1 | 10/2013 | Argentine |
| 2013/0297011 A1 | 11/2013 | Morris et al. |
| 2014/0135909 A1* | 5/2014 | Carr ................... A61F 2/2436 623/2.11 |

FOREIGN PATENT DOCUMENTS

| | | |
|---|---|---|
| EP | 1157673 A2 | 11/2001 |
| EP | 1926455 A2 | 6/2008 |
| WO | 02067782 A2 | 9/2002 |
| WO | 07071436 A2 | 6/2007 |
| WO | 08070797 A2 | 6/2008 |

(56) References Cited

FOREIGN PATENT DOCUMENTS

| WO | 2010042950 A2 | 4/2010 |
| WO | 10051025 A1 | 5/2010 |
| WO | 10087975 A1 | 8/2010 |

OTHER PUBLICATIONS

Duaden, René et al., "Percutaneous aortic valve replacement: resection before implantation," 836-840, European J. of Cardio-thoracic Surgery 27 (2005).

Ruiz, Carlos, "Overview of PRE-CE Mark Transcatheter Aortic Valve Technologies", Euro PCR, May 25, 2010.

\* cited by examiner

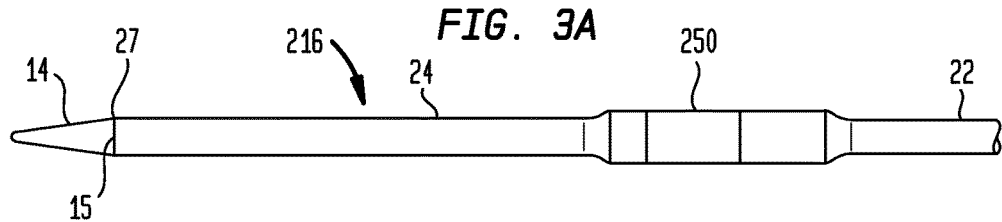
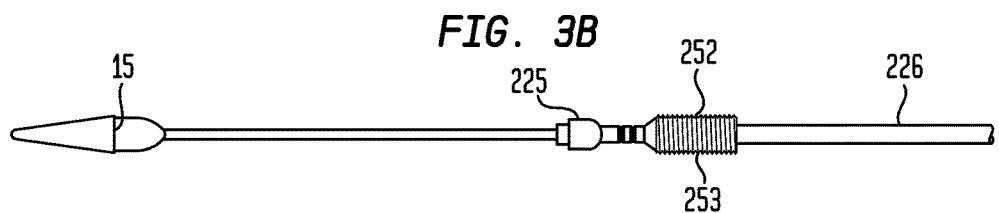
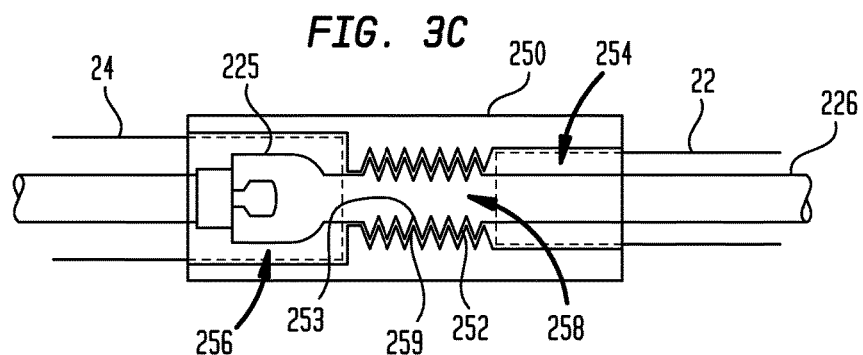
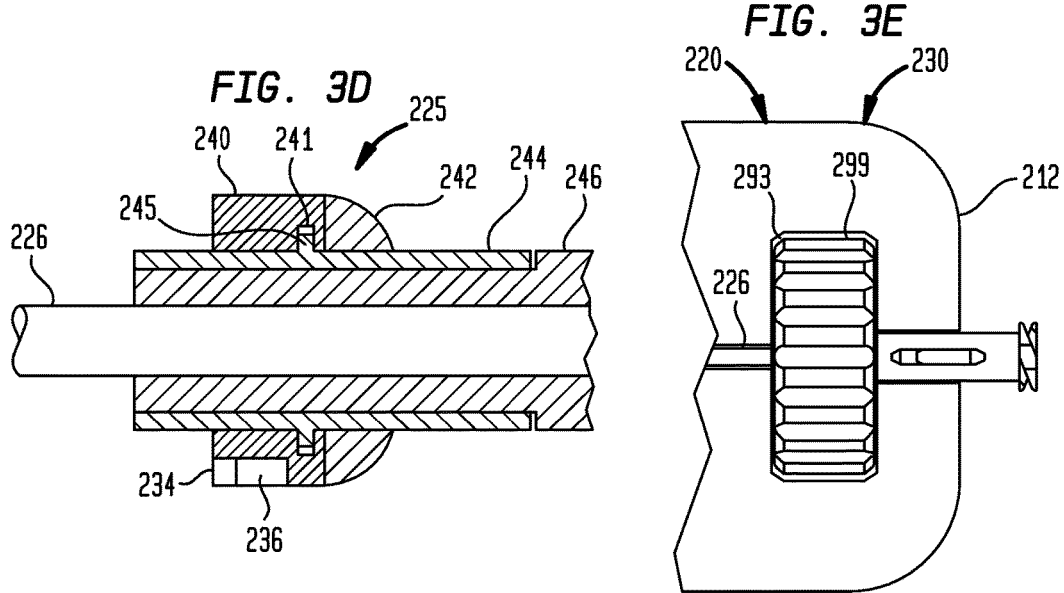

ATRAUMATIC INTERFACE IN AN IMPLANT DELIVERY DEVICE

CROSS-REFERENCE TO RELATED APPLICATIONS

The present application is a national phase entry under 35 U.S.C. § 371 of International Application No. PCT/US2014/054950 filed Sep. 10, 2014, published in English, which claims the benefit of the filing date of U.S. Provisional Patent Application No. 61/877,104 filed Sep. 12, 2013, the disclosures of which are hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheaths the annulus end of the valve, so that the valve can be repositioned while in a collapsed state. After the valve has been repositioned, the user can again release the valve.

Once a self-expanding valve has been fully deployed, it expands to a diameter larger than that of the sheath that previously contained the valve in the collapsed condition, making resheathing impossible, or difficult at best. In order for the user to be able to resheath a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings. For example, in conventional delivery devices for self-expanding valves, it is difficult to completely resheath the valve after partial deployment of the valve, due to axial compression of the distal sheath during the resheathing process.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

Described herein is a delivery device for a collapsible prosthetic heart valve. The delivery device may include an operating handle having a housing and a carriage selectively fixed or movable relative to the housing, and a catheter assembly. The catheter assembly may include an inner shaft around which a compartment is defined, the inner shaft being operatively connected to the housing, the compartment being adapted to receive the valve in an assembled condition.

The catheter assembly may also include an outer shaft surrounding at least a portion of the inner shaft, the outer shaft being fixedly connected to the carriage and movable relative to the inner shaft and the housing, the outer shaft having a compressed length and an extended length greater than the compressed length along an axis of elongation of the outer shaft, a distal sheath fixedly connected to the outer shaft, the distal sheath being movable between a closed condition covering the compartment and an open condition uncovering the compartment for deployment of the valve, and a mechanism configured to apply a distal force to the outer shaft while the carriage is fixed relative to the housing to stretch the outer shaft from the compressed length to the extended length.

Also described herein is another delivery device for a collapsible prosthetic heart valve. The delivery device may include an operating handle having a housing and a carriage selectively fixed or movable relative to the housing, and a catheter assembly. The catheter assembly may include an inner shaft around which a compartment is defined, the inner shaft being configured to be selectively coupled to and uncoupled from the housing, the compartment being adapted to receive the valve in an assembled condition.

The catheter assembly may also include an outer shaft surrounding at least a portion of the inner shaft, the outer shaft being fixedly connected to the carriage and movable relative to the inner shaft and the housing, the outer shaft having a compressed length and an extended length greater than the compressed length along an axis of elongation of the outer shaft, a distal sheath fixedly connected to the outer shaft, the distal sheath being movable between a closed condition covering the compartment and an open condition uncovering the compartment for deployment of the valve, and a mechanism configured to permit movement of the inner shaft relative to the outer shaft and the housing within a predetermined limit in distal and proximal directions.

Also described herein is a method of fully enclosing a compartment of delivery device for implanting a medical device in a patient. The method may include providing the delivery device having a catheter assembly and an operating handle, the operating handle having a housing and a carriage selectively longitudinally fixed or movable relative to the housing, the catheter assembly including an inner shaft around which a medical device compartment is defined, an outer shaft surrounding at least a portion of the inner shaft, and a distal sheath fixedly connected to the outer shaft, the distal sheath being movable between a fully closed condition covering the compartment and an open condition uncovering the compartment.

The method may also include applying a distal force to the outer shaft while the carriage and the inner shaft are longitudinally fixed relative to the housing, thereby stretching the outer shaft from a compressed length to an extended length greater than the compressed length and moving the distal sheath to the fully closed condition, such that a distal end of the distal sheath contacts a proximally-facing abutment surface of the delivery device.

Also described herein is another method of fully enclosing a compartment of delivery device for implanting a medical device in a patient. The method may include providing the delivery device having a catheter assembly and an operating handle, the operating handle having a housing and a carriage selectively longitudinally fixed or movable relative to the housing, the catheter assembly including an inner shaft around which a medical device compartment is defined and configured to be selectively coupled to and uncoupled from the housing, an outer shaft surrounding at least a portion of the inner shaft, and a distal sheath fixedly connected to the outer shaft, the distal sheath being movable between a fully closed condition covering the compartment and an open condition uncovering the compartment.

The method may also include decoupling the inner shaft from the housing so that the inner shaft is movable relative to the housing, and pumping the inner shaft relative to the outer shaft and the housing while the carriage is fixed relative to the housing, thereby reducing compression of the outer shaft so that the outer shaft lengthens from a compressed length to extended length greater than the compressed length and moving the distal sheath to the fully closed condition, such that a distal end of the distal sheath contacts a proximally-facing abutment surface of the delivery device.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIG. 3A is a side view of a portion of another catheter assembly suitable for use with the delivery device of FIG. 1A;

FIG. 3B is a side view of a portion of the inner shaft in the catheter assembly of FIG. 3A;

FIG. 3C is an enlarged schematic longitudinal cross-section of the transition piece in the catheter assembly of FIG. 3A;

FIG. 3D is an enlarged longitudinal cross-section of the retainer in the catheter assembly of FIG. 3A;

FIG. 3E is an enlarged top plan view of an inner shaft rotational actuator suitable for use with the catheter assembly of FIG. 3A;

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user. As used herein, the terms "generally," "substantially," "approximately," and "about" are intended to mean that slight deviations from absolute are included within the scope of the term so modified.

Figure 1A:
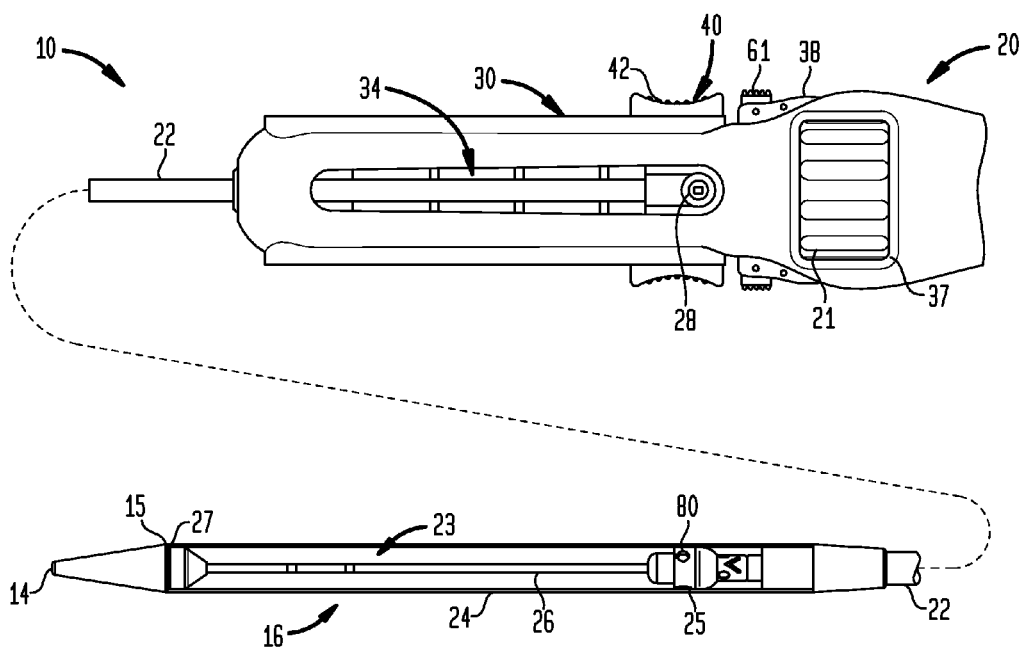
FIG. 1A is a top plan view of a portion of an operating handle for a transfemoral delivery device for a collapsible prosthetic heart valve, shown with a partial longitudinal cross-section of the distal portion of a transfemoral catheter assembly.
Figure 1B:
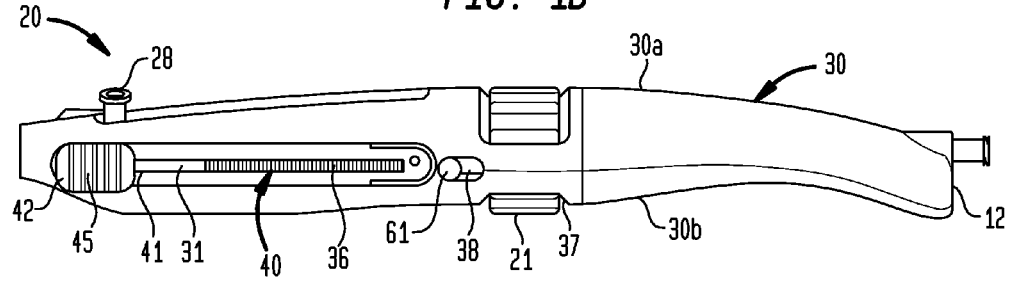
FIG. 1B is a side view of the handle of FIG. 1A.

Referring now to FIGS. 1A and 1B to illustrate the structure and function of the present invention, an exemplary transfemoral delivery device 10 for a collapsible prosthetic heart valve (or other types of implantable medical devices) has a catheter assembly 16 for delivering the heart valve to and deploying the heart valve at a target location, and an operating handle 20 for controlling deployment of the valve from the catheter assembly. The delivery device 10 extends from a proximal end 12 (FIG. 1B) to an atraumatic tip 14 at the distal end of catheter assembly 16. The catheter assembly 16 is adapted to receive a collapsible prosthetic heart valve (not shown) in a compartment 23 defined around an inner shaft 26 and covered by a distal sheath 24.

The inner shaft 26 may extend through the operating handle 20 and the catheter assembly 16 to the atraumatic tip 14 of the delivery device, and includes a retainer 25 affixed thereto at a spaced distance from the atraumatic tip 14 and adapted to hold a collapsible prosthetic valve in the compartment 23. The inner shaft 26 may be made of a flexible material such as braided polyimide or polyetheretherketone (PEEK), for example. Using a material such as PEEK may improve the resistance of the inner shaft 26 to kinking while the catheter assembly 16 is tracking through the vasculature of a patient. The retainer 25 may have recesses 80 therein that are adapted to hold corresponding retention members of the valve.

The distal sheath 24 surrounds the inner shaft 26 and is slidable relative to the inner shaft such that it can selectively cover or uncover the compartment 23. The distal sheath 24 is affixed at its proximal end to an outer shaft 22, the proximal end of which is connected to the operating handle 20 in a manner to be described. The distal end 27 of the distal sheath 24 abuts a proximally-facing abutment surface 15 of the atraumatic tip 14 when the distal sheath is fully covering the compartment 23, and is spaced apart from the proximally-facing abutment surface when the compartment 23 is at least partially uncovered.

The operating handle 20 is adapted to control deployment of a prosthetic valve located in the compartment 23 by permitting a user to selectively slide the outer shaft 22 proximally or distally relative to the inner shaft 26, thereby respectively uncovering or covering the compartment with the distal sheath 24. The outer shaft 22 may be made of a flexible material such as nylon 11 or nylon 12, and it may have a round braid construction (i.e., round cross-section fibers braided together) or flat braid construction (i.e., rectangular cross-section fibers braided together), for example.

The proximal end of the inner shaft 26 may be connected in substantially fixed relationship to an outer housing 30 of the operating handle 20 (the longitudinal position of the inner shaft relative to the housing may be movable in some embodiments, for example, as described below with reference to FIGS. 3A through 4C), and the proximal end of the outer shaft 22 may be affixed to a carriage assembly 40 that is slidable along a longitudinal axis of the handle housing, such that a user can selectively slide the outer shaft relative to the inner shaft by sliding the carriage assembly relative to the housing. A hemostasis valve 28 includes an internal gasket adapted to create a seal between the inner shaft 26 and the proximal end of the outer shaft 22.

The handle housing 30 defines an elongated space 34 in which the carriage assembly 40 may travel. The elongated space 34 preferably permits the carriage assembly 40 to travel a distance that is at least as long as the anticipated length of the prosthetic valve to be delivered (e.g., at least about 50 mm), such that the distal sheath 24 can be fully retracted from around the prosthetic valve. A pair of slots 31 may be formed on opposite sides of the housing 30, contiguous with the elongated space 34. The length of the slots 31, minus the width of the carriage grip shafts (not shown), determines the maximum distance that the carriage assembly 40 can travel within the space 34.

The carriage assembly 40 has a body portion 41 with a threaded rod 36 extending proximally therefrom along the longitudinal axis of the housing 30. The housing 30 defines an elongated bore (not shown) that is sized to freely and slidingly receive the threaded rod 36. The elongated bore has an inner diameter slightly larger than the outer diameter of the threaded rod 36. The threaded rod 36 preferably is longer than the anticipated maximum travel distance of the carriage assembly 40 within the elongated space 34 (e.g., at least about 50 mm), such that the threaded rod 36 does not fully disengage from the deployment actuator 21 (described below) during sheathing or resheathing of the prosthetic valve.

The carriage assembly 40 further includes a pair of carriage grips 42 each attached to the body portion 41 by a respective carriage grip shaft (not shown). Although the carriage assembly 40 is shown in FIGS. 1A and 1B as having two carriage grips 42, that need not be the case; and the carriage assembly 40 may have only a single carriage grip 42. As shown in FIG. 1B, the lateral sides of the carriage grips 42 may include a plurality of parallel ridges 45 to facilitate grasping and moving of the carriage grips.

The handle housing 30 further defines a pocket 37 that extends through the top portion 30*a* and bottom portion 30*b* for receiving the deployment actuator 21. The deployment actuator 21 is internally threaded for selective engagement with the threaded rod 36. The pocket 37 is sized and shaped to receive the deployment actuator 21 with minimal clearance, such that the location of the deployment actuator remains substantially fixed relative to the housing 30 as it is rotated about the threaded rod 36. That is, when the deployment actuator 21 is in threaded engagement with the threaded rod 36, rotation of the deployment actuator in one direction (either clockwise or counterclockwise depending on the orientation of the threads on the threaded rod) causes the threaded rod to move proximally within the elongated bore, at the same time pulling the body portion 41 of the carriage assembly 40 proximally through the elongated space 34. Similarly, when the deployment actuator 21 is in threaded engagement with the threaded rod 36, rotation of the deployment actuator in the opposite direction causes the threaded rod to move distally within the elongated bore, at the same time pushing the body portion 41 of the carriage assembly 40 distally through the elongated space 34.

The deployment actuator 21 may be selectively placed in threaded engagement with the threaded rod 36 by a coupling assembly. A pair of buttons 61 positioned on opposite lateral sides of the coupling assembly may be slidably received in longitudinal openings 38 formed on opposite lateral sides of the housing 30. Actuation of the buttons 61 causes a split nut (not shown) to engage or disengage from the threaded rod 36, thereby selectively coupling or decoupling the deployment actuator 21 from the threaded rod. For example, when the buttons 61 are in a proximal position within the longitudinal openings 38, rotation of the deployment actuator 21 translates the threaded rod 36, and when the buttons are in a distal position within the longitudinal openings, the threaded rod may be translated without rotation of the deployment actuator, by a user grasping and moving the carriage grips 42.

The handle 20 may also include a resheathing lock adapted to limit the longitudinal movement of the carriage assembly 40 proximally within the handle housing 30, thereby preventing the user from completing the deployment of a prosthetic valve unintentionally. The initial distance that the carriage assembly 40 can travel before being limited by the resheathing lock may depend on the structure of the particular prosthetic valve to be deployed. Preferably, the initial travel distance of the carriage assembly 40 is about 3 mm to about 5 mm less than the crimped valve length. Alternatively, the initial travel distance of the carriage assembly 40 may be about 40 mm to about 45 mm, which is about 80% to about 90% of the length of an exemplary 50 mm valve. The initial distance that the carriage assembly 40 can travel may be determined as a percentage of the length of the prosthetic valve and/or the compartment 23, including, for example, 50%, 60%, 70%, 75%, 85%, or 95%.

Further details of the coupling assembly and embodiments of resheathing locks suitable for use with the delivery device 10 are shown and described in co-pending and co-owned U.S. patent application Ser. No. 13/788,820, the disclosure of which is hereby incorporated by reference herein.

The operation of the delivery device 10 of FIGS. 1A and 1B to deploy a prosthetic valve will now be described. To load the delivery device 10 with a collapsible prosthetic valve, the user may place the buttons 61 in the distalmost position within the openings 38 to disengage the deployment actuator 21 from the threaded rod 36. The carriage grips 42 may then be slid proximally relative to the slots 31 to move the carriage assembly 40 proximally and thereby retract the distal sheath 24 and expose the compartment 23. A compressed or crimped valve may then be loaded around the inner shaft 26, and the proximal end of the valve may be coupled to the retainer 25. The carriage grips 42 may then be slid in the opposite or distal direction relative to the slots 31 to move the carriage assembly 40 distally and cover the compartment 23 with the distal sheath 24 to hold the valve in the compressed state.

The buttons 61 may then be placed in the starting condition of the delivery device 10. In this starting condition, the handle 20 will be in an initial state with the carriage assembly 40 at its distalmost position within the handle housing 30, and the buttons 61 will each be at the proximalmost position within the respective openings 38, such that the deployment actuator 21 is threadedly engaged with the threaded rod 36.

To use the operating handle 20 to deploy a prosthetic valve that has been loaded into the compartment 23 and covered by the distal sheath 24, the user may rotate the deployment actuator 21, causing the carriage assembly 40 to slide proximally within the elongated space 34 in the housing 30. Because the distal sheath 24 is affixed to the outer shaft 22, which in turn is affixed to the carriage assembly 40, and because the inner shaft 26 is fixed to the housing 30, sliding the carriage assembly proximally relative to the housing will retract the distal sheath proximally from the compartment 23, thereby exposing and initiating deployment of the valve located therein.

When the deployment procedure has reached a partial deployment of the valve, for example, deployment of about 80% of the length of the valve, the user can evaluate the position of the valve relative to the patient's aortic annulus and may be able to determine whether the valve is functioning properly. If repositioning or removal is desired, with the buttons 61 positioned to engage the deployment actuator 21 with the threaded rod 36, the user may resheath the valve by rotating the deployment actuator 21 in the direction opposite that used for deployment. Such rotation will cause the threaded rod 36 to progress distally through the deployment actuator 21 until the carriage assembly 40 has reached the starting position shown in FIG. 1B, thereby re-collapsing the expanded part of the valve as the distal sheath 24 is moved distally over the compartment 23 and the partially deployed valve. With the valve resheathed, the user can reposition the delivery device 10 and commence the deployment procedure once again or simply remove the valve from the patient.

Once the proper positioning of the valve relative to the aortic annulus has been assured, the user may complete the deployment process. The user can slide the carriage assembly proximally to complete the deployment of the valve by rotating the deployment actuator 21. When the valve has been completely unsheathed, the stent portion of the valve self-expands and disengages from the retainer 25, thereby releasing the valve from the catheter assembly 16.

The inventors have found that during operation of the delivery device 10 to deploy a prosthetic valve, if it becomes necessary to resheath the valve during deployment, axial compressive forces are applied to the outer shaft 22 during the resheathing process. As used herein with respect to an elongated shaft such as the outer shaft 22, "axial" compression or compressive forces are understood to be acting along a longitudinal axis extending in the elongation direction of the shaft. Such axial compressive forces acting on the outer shaft 22 may arise from friction between the valve and the distal sheath 24, which is affixed at its proximal end to the outer shaft, or from friction between the outer shaft and one or both of the inner shaft 26 and the native anatomy of the patient.

Axial compression of the outer shaft 22 may result in an inability of the distal sheath 24 to completely cover the compartment 23 in the closed position. That is, the distal sheath may not extend far enough for its distal end 27 to abut the proximally-facing abutment surface 15 of the atraumatic tip 14. Having a gap between the distal end 27 of the distal sheath 24 and the proximally-facing abutment surface 15 is undesirable during movement of the catheter assembly 16 inside the native anatomy of a patient because native tissue may become lodged between the distal end of the distal sheath and the atraumatic tip, or may be abraded by the distal end of the distal sheath.

The inventors have found that the compressive forces applied to the outer shaft 22 during the resheathing process may temporarily axially compress the outer shaft between about 1 mm and about 15 mm, or more typically, between about 5 mm and about 10 mm. Such temporary axial compression of the outer shaft 22 during the resheathing process may sometimes be relieved in about 10 to about 15 minutes by the shape memory of the outer shaft acting to restore the outer shaft to its initial length. However, such a waiting time may be undesirable or not possible during deployment of a valve into a patient. In such circumstances, one or more of the embodiments shown and described below with respect to FIGS. 2A through 5E may be used to quickly remove such temporary axial compression of the outer shaft 22 without removing the delivery device 10 from a patient.

Figure 2A:
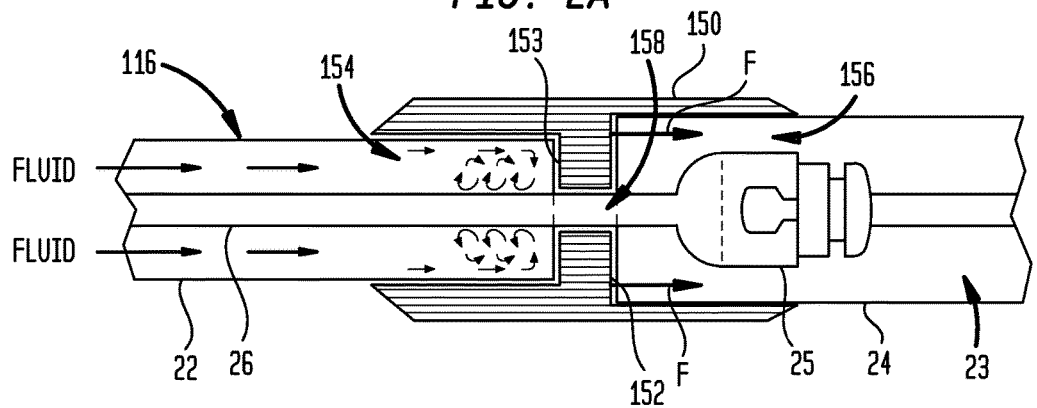
FIG. 2A is a longitudinal cross-section of a portion of a catheter assembly suitable for use with the delivery device of FIG. 1A, shown with a side view of the retainer.

Referring now to FIG. 2A, a catheter assembly 116 suitable for use with the delivery device 10 of FIG. 1A is the same as the catheter assembly 16 described above, except that the catheter assembly 116 includes a transition piece 150 having a fluid dam 152, and the proximal end of the outer shaft 22 is in fluid communication with a pressurized fluid source, for example, pressurized saline. The pressure source may be a conventional medical balloon inflator (not shown), such as an angioplasty balloon inflator, which is configured to provide a pressurized fluid inside the outer shaft 22.

In one example, the fluid may be provided at a pressure of at least 80 psi. In another example, the fluid may be provided at a pressure of at least 100 psi. The aforementioned pressure examples are to be understood merely as non-limiting examples. Other pressures may be used, depending on the design of the delivery device and the catheter assembly, and/or depending on the type and size of implantable medical device to be deployed.

The transition piece 150 affixes the proximal end of the distal sheath 24 to the distal end of the outer shaft 22, providing a smooth transition between the confronting ends of the distal sheath and the outer shaft, which may have different diameters. For example, the diameter of the outer shaft 22 may be 13 French (4.3 mm), while the diameter of the distal sheath may be 18 French (6.0 mm). The transition piece 150 has a proximal recess 154 sized to receive the distal end of the outer shaft 22, and a distal recess 156 opposite the proximal recess sized to receive the proximal end of the distal sheath 24.

The fluid dam 152 separates the proximal recess 154 from the distal recess 156. The fluid dam 152 has a proximal-facing surface 153 and a central opening 158 that is sized to slidably receive the inner shaft 26 therethrough. The opening 158 preferably has a diameter that is greater than the diameter of the inner shaft 26, but close enough to the diameter of the inner shaft to entirely or almost entirely block fluid flow through the circumferential gap between the fluid dam 152 and the inner shaft. For example, the opening 158 may have a diameter that is about 0.5 mm greater than the diameter of the inner shaft 26.

During the placement of a prosthetic valve into a patient, when a valve contained within the compartment 23 of the catheter assembly 116 is partially deployed and then resheathed, the temporary axial compression of the outer shaft 22 may cause a gap to remain between the distal end 27 of the distal sheath 24 and the proximally-facing abutment surface 15 of the atraumatic tip 14 when the distal sheath is in its distalmost position (e.g., a gap of about 1 mm to about 15 mm), such that the distal sheath is in a partially closed condition covering a major portion of the compartment. As used herein, when a distal sheath covers a "major portion" of a compartment, that means more than half of a valve or other medical device within the compartment is covered by the distal sheath.

To axially stretch the outer shaft 22 to relieve such temporary axial compression, a user may provide a pressurized fluid to the proximal end of the outer shaft. The pressurized fluid within the outer shaft 22 will provide a force F to the fluid dam 152 in an axial direction of the outer shaft. Since the transition piece 150 is fixedly connected to the distal end of the outer shaft 22 and is configured to be slidable along the inner shaft 26, the force F acting on the fluid dam 152 will cause the transition piece to move in a distal direction toward the retainer 25, thereby axially stretching the outer shaft 22 and closing the gap between the distal end 27 of the distal sheath 24 and the proximally-facing abutment surface 15. After the outer shaft 22 is stretched enough so that the gap between the distal end 27 of the distal sheath 24 and the proximally-facing abutment surface 15 is closed, the pressure within the outer shaft may be relieved.

If the valve contained within the compartment 23 of the catheter assembly 116 is once again partially deployed and then resheathed during the same valve deployment procedure, thereby re-creating temporary axial compression of the outer shaft 22, the aforementioned process of axially stretching the outer shaft may be repeated to relieve such compression.

Figure 2B:
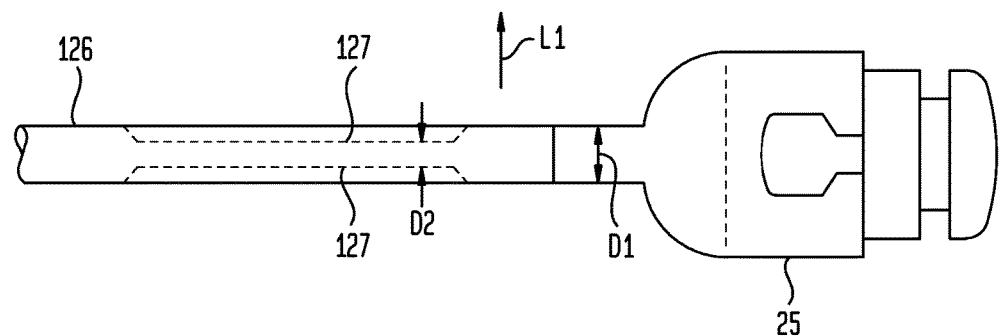
FIG. 2B is an enlarged side view of a portion of the inner shaft and retainer in a variant of the catheter assembly of FIG. 2A.

Referring now to FIG. 2B, an inner shaft 126 suitable for use with the catheter assembly 116 of FIG. 2A is the same as the inner shaft 26 described above, except that the inner shaft 126 includes one or more recessed portions 127. The recessed portions 127 are configured to provide one or more regions of extra fluid volume within the outer shaft 22 at a location close to the fluid dam 152. Such extra volume may allow a given force F to be provided to the fluid dam 152 in an axial direction of the outer shaft using a lower fluid pressure within the outer shaft 22 than in the embodiment of FIG. 2A.

In the example shown in FIG. 2B, there are flattened recessed portions 127 on opposite sides of the inner shaft 126 that reduce the overall diameter D1 of the inner shaft 126 to a diameter D2 in a first direction through the recessed portions. However, the recessed portions do not extend around the entire circumference of the inner shaft 126, such that the inner shaft has the diameter D1 in a direction perpendicular to the first direction. Alternatively, the inner shaft 126 may have any number of recessed portions of any shape that provide one or more regions of extra fluid volume within the outer shaft 22. The recessed portions 127 may be symmetrically or asymmetrically disposed about the circumference of the inner shaft 126, and need not be at the same positions along the length of the inner shaft.

Figure 2C:
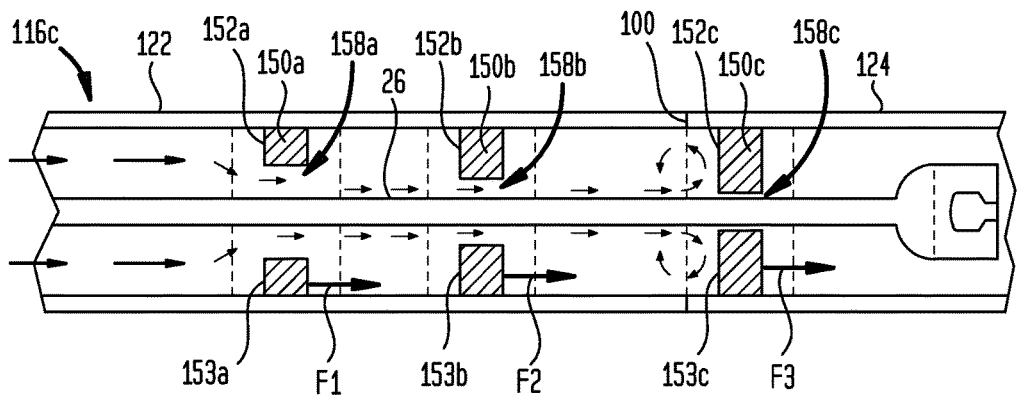
FIG. 2C is a longitudinal cross-section of a variant of the catheter assembly of FIG. 2A, having a plurality of fluid dams.

Referring now to FIG. 2C, a catheter assembly 116c suitable for use with the delivery device 10 of FIG. 1A is the same as the catheter assembly 116 described above, except that the catheter assembly 116c includes a plurality of dam inserts 150a, 150b, and 150c, two of the inserts being disposed within the distal end of the outer shaft 122, and one of the inserts being disposed within the proximal end of the distal sheath 124 adjacent the location 100 where the outer shaft abuts the distal sheath.

As shown in FIG. 2C, each of the dam inserts 150a, 150b, and 150c has a progressively smaller opening 158a, 158b, and 158c, respectively, compared to the adjacent proximal insert. For example, the first dam insert 150a has an opening 158a that may be about 1.5 mm greater than the diameter of the inner shaft 26, the second dam insert 150b has an opening 158b that may be about 1.0 mm greater than the diameter of the inner shaft, and the third dam insert 150c has an opening 158c that may be about 0.5 mm greater than the diameter of the inner shaft. The first and second openings 158a and 158b are configured to permit some fluid flow therethrough, but the third opening 158c is configured to entirely or almost entirely block fluid flow therethrough, while still permitting the inner shaft to be slideable therethrough. Each of the dam inserts 150a, 150b, and 150c has a progressively larger proximal-facing surface 153a, 153b, and 153c, respectively, compared to the adjacent proximal insert.

In use, the pressurized fluid within the outer shaft 122 may provide a force to each of the dam inserts 150a, 150b, and 150c in an axial direction of the outer shaft. However, since the openings 158a, 158b, and 158c get progressively smaller in the distal direction such that a progressively larger dam surface 152a, 152b, and 152c faces in a proximal direction, fluid in the outer shaft 122 at a given pressure may generate a force F1 at the first dam insert 150a, a force F2 at the second dam insert 150b greater than the force F1, and a force F3 at the third dam insert 150c greater than the force F2. For a given fluid pressure inside the outer shaft, the sum of the forces F1, F2, and F3 acting on the three dam inserts 150a, 150b, and 150c of FIG. 2C may exceed the force F acting on the single transition piece 150 of FIG. 2A.

Referring now to FIGS. 3A-3C, a catheter assembly 216 suitable for use with the delivery device 10 of FIG. 1A is the same as the catheter assembly 16 described above, except that the catheter assembly 216 includes a threaded transition piece 250 configured to receive a threaded portion 252 of a rotatable inner shaft 226, and a portion of the retainer 225 is freely rotatable about the inner shaft so that when the inner shaft rotates, friction between the valve and the distal sheath 24 prevents the valve and the retainer 225 from rotating with the inner shaft.

The transition piece 250 affixes the proximal end of the distal sheath 24 to the distal end of the outer shaft 22, providing a smooth transition between the confronting ends of the distal sheath and the outer shaft, which may have different diameters. The transition piece 250 has a proximal recess 254 sized to receive the distal end of the outer shaft 22, and a distal recess 256 opposite the proximal recess sized to receive the proximal end of the distal sheath 24.

The transition piece 250 has an intermediate portion 258 extending between the proximal recess 254 and the distal recess 256. The intermediate portion 258 has threads 259 that are configured to mate with corresponding threads 253 of the threaded portion 252 of the rotatable inner shaft 226. The threaded portion 252 of the rotatable inner shaft 226 may be affixed to or formed integrally with the inner shaft, so that rotation of the inner shaft also rotates the threaded portion.

The longitudinal length of the threads 253 of the threaded portion 252 and the longitudinal length of the threads 259 of the intermediate portion 258 preferably are slightly longer than the maximum anticipated temporary axial compression of the outer shaft 22, such as about 15 mm, for example.

Referring now to FIG. 3D, the retainer 225 includes an outer piece 240, a support piece 242 located adjacent to the outer piece, and an inner piece 244 that is coupled to the outer piece so as to be rotatable relative thereto. The inner piece 244 is affixed to a stiffening member 246, which in turn is affixed to the inner shaft 226. The outer piece 240 and the support piece 242 may be attached together (e.g., via welding or any other known joining technique) so that they are rotatable together relative to the inner piece 244, or the support piece may be attached to the inner piece, such that the outer piece may rotate relative to both the support piece and the inner piece.

The outer piece 240 includes one or more recesses 236, each of which is located at the retention edge 234 of the outer piece and configured to receive a corresponding retention member of the stent portion of a collapsible valve. Each recess 236 preferably has a similar shape and a slightly larger size than a conventional stent retention member so as to capture same readily, but with only a small amount of relief therebetween. Forming recesses 236 with an appropriate shape and size prevents longitudinal movement of the valve within the valve receiving compartment 23, such as during deployment or resheathing procedures.

The inner piece 244 includes an annular ring 245 that is adapted to fit into a corresponding circumferential groove 241 defined in the outer piece 240. The ring 245 and the groove 241 are configured to enable the outer piece 240 to freely rotate about the inner piece 244 but not to slide longitudinally by any significant amount relative to the inner piece. In the embodiment shown, a small amount of longitudinal movement is permitted between the outer piece 240 and the inner piece 244 so as to minimize frictional braking forces between these elements, but the ring 245 and the groove 241 retain the outer piece 240 on the inner piece 244 during use of the retainer 225.

FIG. 3E shows a proximal end 212 of a handle housing 230 that is a variation of the proximal end 12 of the handle housing 30 of FIGS. 1A and 1B, such variation permitting rotation of the inner shaft 226 relative to the handle housing and relative to the outer shaft 22.

A pocket 293 extends vertically into or through the handle housing 230 for receiving an inner shaft rotational actuator 299 that is affixed to the inner shaft 226 for rotation therewith. The pocket 293 is sized and shaped to receive the shaft rotational actuator 299 with minimal clearance, such that the rotational actuator remains substantially longitudinally fixed relative to the handle housing 230 as it rotates.

When the threads 253 of the threaded portion 252 of the inner shaft 226 are engaged with the threads 258 of the transition piece 250, rotation of the rotational actuator 299 in one direction (either clockwise or counterclockwise depending on the orientation of the threads of the threaded portion) causes the transition piece to move proximally relative to the handle housing and the inner shaft, and rotation of the rotational actuator in the opposite direction causes the transition piece to move distally relative to the handle housing and the inner shaft.

Referring to FIGS. 3A-3E, after loading a prosthetic valve into the compartment 23 and covering the valve with the distal sheath 24, the intermediate portion 258 of the transition piece 250 is initially fully threadedly engaged with the threaded portion 252 of the inner shaft 226. To use the catheter assembly 216 to deploy the prosthetic valve, the user may position the buttons 61 at their distal position so that the threaded rod 36 is decoupled from the deployment actuator 21 (FIG. 1A), and the user may rotate the rotational actuator 299 in a first rotational direction to rotate the inner shaft 226 and the threaded portion 252 thereof. Because of the threaded engagement between the threaded portion 252 and the intermediate portion 258 of the transition piece 250, and because the inner shaft 226 is not able to move in a longitudinal direction relative to the handle 20, this rotation of the inner shaft and the threaded portion will move the transition piece, the outer shaft 22, and the distal sheath 24 proximally relative to the inner shaft, thereby beginning to uncover the compartment 23. Once the intermediate portion 258 of the transition piece 250 is no longer coupled to the threaded portion 252 of the inner shaft 226, the user may continue deployment of the valve in the same way as described above with reference to FIGS. 1A and 1B.

Similar to the embodiment of FIG. 2A, when a valve contained within the compartment 23 of the catheter assembly 216 is partially deployed and then resheathed, the temporary axial compression of the outer shaft 22 may cause a gap to remain between the distal end 27 of the distal sheath 24 and the proximally-facing abutment surface 15 of the atraumatic tip 14 when the distal sheath is in its distalmost position (e.g., a gap of about 1 mm to about 15 mm), such that the distal sheath is in a partially closed condition covering a major portion of the compartment. However, since the longitudinal lengths of the threaded portion 252 and the intermediate portion 258 are slightly longer than the maximum anticipated temporary axial compression of the outer shaft 22, the proximal end of the threaded portion will still be able to engage the distal end of the intermediate portion of the transition piece, although complete engagement of the mating threads may not be possible without lengthening of the outer shaft 22 to its initial length.

To axially stretch the outer shaft 22 to relieve the temporary axial compression thereof, the user may position the buttons 61 at their proximal position so that the threaded rod 36 is coupled to the deployment actuator 21 (FIG. 1A), and the user may rotate the rotational actuator 299 in a second rotational direction opposite the first rotational direction to move the transition piece 250 distally relative to the threaded portion 252 of the inner shaft 226, thereby axially stretching the outer shaft and moving the distal sheath 24 in a distal direction. Once the intermediate portion 258 of the transition piece 250 is fully threadedly engaged into the threaded portion 252 of the inner shaft 226, the distal end 27 of the distal sheath 24 will abut the proximally-facing abutment surface 15, thereby completely covering the compartment 23.

If the valve contained within the compartment 23 of the catheter assembly 216 is once again partially deployed and then resheathed during the same valve deployment procedure, thereby re-creating temporary axial compression of the outer shaft 22, the aforementioned process of axially stretching the outer shaft may be repeated to relieve such compression.

Although the catheter assembly 216 is shown and described as having threads 253 of the threaded portion 252 and threads 259 of the intermediate portion 258 each having a longitudinal length slightly longer than the maximum anticipated temporary axial compression of the outer shaft 22, and being fully threadedly engaged with one another when the distal sheath 24 completely covers the compartment 23, that need not be the case. Also, although the catheter assembly 216 is shown and described as having the threads 253 and 259 located between the outer shaft 22 and the distal sheath 24 when the distal sheath 24 completely covers the compartment 23, that need not be the case.

Alternatively, the threads 253 of the threaded portion 252 and the threads 259 of the intermediate portion 258 may each have any longitudinal length and any longitudinal position, equal or unequal in length to one another, as long as: (1) the threads 253 and 259 are at least partially engaged with one another when the distal sheath 24 completely covers the compartment 23, to ensure that the compartment can be completely closed by the axial stretching process; (2) the distance between the distal end of the threads 259 and the proximal end of the threads 253 is slightly greater than the maximum anticipated temporary axial compression of the outer shaft 22, to ensure that the threads 253 and 259 can be at least partially engaged when the outer shaft has been axially compressed to the maximum anticipated amount; and (3) the threads 253 and 259 are located distally of the distal end of the outer shaft 22 or close to the distal end of the outer shaft, to ensure that all or substantially all of the outer shaft 22 will be stretched during the axial stretching process described above.

Figure 4A:
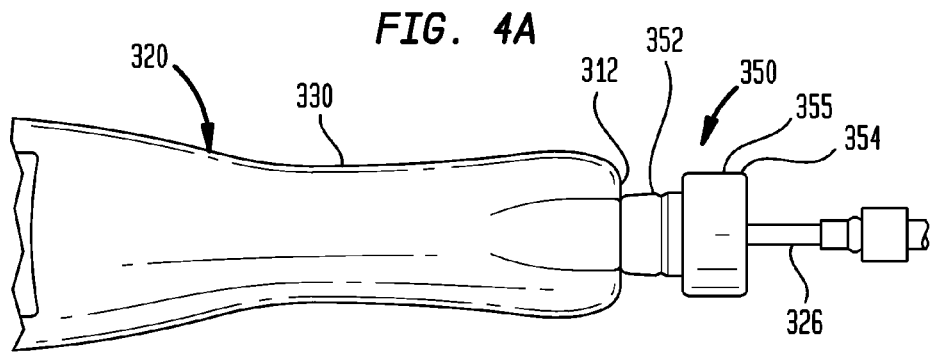
FIG. 4A is a side view of a portion of an inner shaft decoupling assembly suitable for use with the delivery device of FIG. 1A.
Figure 4B:
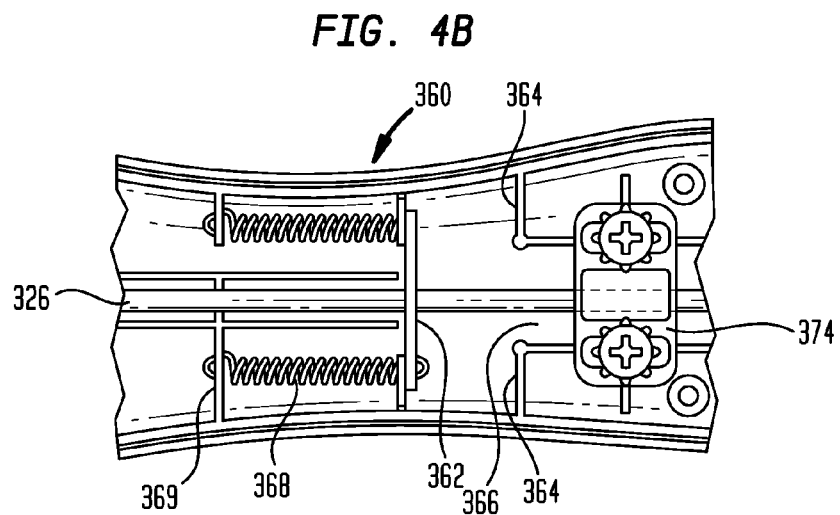
FIG. 4B is an enlarged top view of a portion of the handle housing of FIG. 4A, with the top portion removed to show a distal limiting assembly suitable for use with the inner shaft decoupling assembly of FIG. 4A.
Figure 4C:
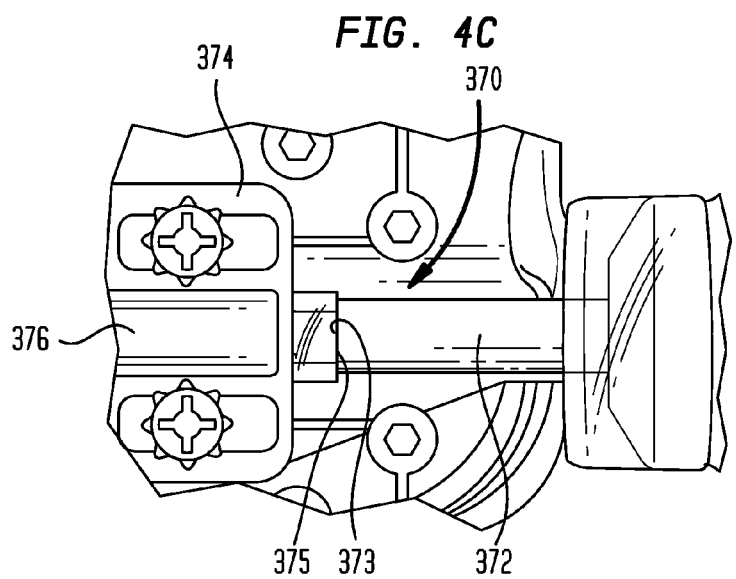
FIG. 4C is an enlarged top view of a portion of the handle housing of FIG. 4A, with the top portion removed to show a proximal limiting assembly suitable for use with the inner shaft decoupling assembly of FIG. 4A.

FIGS. 4A-4C illustrate an embodiment of an operating handle 320 having an inner shaft decoupling assembly 350 suitable for use with the delivery device of FIGS. 1A and 1B. The handle 320 of FIGS. 4A-4C is the same as the handle 20 described above, except that the inner shaft 326 may be selectively decoupled from the handle housing 330 so that a user may move the inner shaft back and forth relative to the outer shaft 22 to relieve temporary axial compression of the outer shaft, thereby permitting the distal sheath 24 to completely cover the compartment after resheathing. Such temporary axial compression of the outer shaft 22 may result from friction between the valve and the distal sheath 24, which is affixed at its proximal end to the outer shaft, or from friction between the outer shaft and one or both of the inner shaft 326 and the native anatomy of the patient.

The inner shaft decoupling assembly 350 may be a conventional hemostasis valve including an iris seal, although other decoupling mechanisms may be used. The inner shaft decoupling assembly 350 includes a fixed portion 352 that is affixed to the proximal end 312 of the handle housing 330, and a rotatable portion 354 that is engaged with the fixed portion. The fixed portion 352 has a recess that defines an inner circumferential surface having threads formed therein. The rotatable portion 354 has a knob 355 and a nose extending distally from the knob that is configured to extend into the recess, the nose being externally threaded for mating with the threads of the fixed portion 352.

The rotatable portion 354 further includes a circumferentially-extending silicone element (not shown) that surrounds a portion of the inner shaft 326. When the knob 355 is rotated in a first rotational direction, the silicone element is compressed and tightens onto the inner shaft 326, thereby fixing the inner shaft to the handle housing 330. When the knob 355 is rotated in a second rotational direction opposite the first rotational direction, pressure is removed from the silicone element and the silicone element relaxes around the inner shaft 326, thereby freeing the inner shaft to move relative to the handle housing 330.

The handle 320 further includes a distal limiting assembly 360 (FIG. 4B) located distally of the proximal end 312 of the handle housing 330, and a proximal limiting assembly 370 (FIG. 4C) located proximally of the distal limiting assembly, the distal and proximal limiting assemblies configured to limit the range of axial movement of the inner shaft 326 to a desired range. The desired range preferably is approximately equal to the maximum anticipated temporary axial compression of the outer shaft 22, such as about 15 mm, for example. The handle 320 preferably includes a distal limiting assembly 360 so that when a user slides the inner shaft distally as described below, the atraumatic tip 14 does not extend so far distally so as to damage surrounding patient tissue. The handle 320 preferably includes a proximal limiting assembly 370 so that when a user slides the inner shaft proximally as described below, the atraumatic tip 14 does not become wedged too far inside the distal sheath 24 so as to damage the delivery device.

The distal limiting assembly 360 includes a stop plate 362 affixed to the inner shaft 326 and a pair of limiting ribs 364 molded with or otherwise affixed to the handle housing 330. The stop plate 362 is wider than a bore 366 extending between the pair of ribs 364 through which the inner shaft 326 extends, such that movement of the stop plate in a proximal direction will be limited by contact with the pair of ribs. The distal limiting assembly 360 further includes one or more energy storage elements such as springs 368 that extend between attachment ribs 369 of the handle housing 330 and the stop plate 362. The springs 368 are biased to contract along the longitudinal axis of the handle, such that when a user slides the inner shaft 326 proximally from its initial position and then releases the inner shaft, the springs contract to move the inner shaft distally back to its initial or rest position.

The proximal limiting assembly 370 includes a stop sleeve 372 affixed around the inner shaft 326 and a limiting bracket 374 affixed to the handle housing 330. The outer diameter of the stop sleeve 372 is greater than the diameter of a bore 376 extending through the limiting bracket 374 through which the inner shaft 326 extends, such that movement of the stop sleeve in the distal direction will be limited by contact of the distal end 373 of the stop sleeve with the proximal end 375 of the limiting bracket.

In use during placement of a prosthetic valve into a patient, when a valve contained within the compartment 23 of the catheter assembly 16 (FIGS. 1A and 1B) is partially deployed and then resheathed, the temporary axial compression of the outer shaft 22 relative to the inner shaft 326 may cause a gap to remain between the distal end 27 of the distal sheath 24 and the proximally-facing abutment surface 15 of the atraumatic tip 14 when the distal sheath is in its distal-most position (e.g., a gap of about 1 mm to about 15 mm), such that the distal sheath is in a partially closed condition covering a major portion of the compartment.

To relieve temporary axial compression of the outer shaft 22, a user may rotate the knob 355 in a first rotational direction to decouple the inner shaft 326 from the handle housing 330. Then, the user may slide or "pump" the inner shaft 326 back and forth one or more times relative to the outer shaft 22 along the longitudinal axis of the handle 320. In one example, the user may pump the inner shaft 326 back and forth at least two times. The number of times that the user may pump the inner shaft 326 relative to the outer shaft 22 may depend on the anticipated amount of temporary axial compression of the outer shaft.

This pumping motion of the inner shaft 326 may agitate the outer shaft 22 relative to the inner shaft and the native anatomy of the patient, thereby relieving temporary axial compression of the outer shaft. After the pumping motion is completed, the user may rotate the knob 355 in a second rotational direction opposite the first rotational direction to re-couple the inner shaft 326 to the handle housing 330 so that deployment of the valve may be attempted again.

If the valve contained within the compartment 23 of the catheter assembly 16 is once again partially deployed and then resheathed during the same valve deployment procedure, thereby re-creating temporary axial compression of the outer shaft 22, the aforementioned process of pumping the inner shaft 326 may be repeated to relieve such compression.

Referring now to FIGS. 5A-5E, a catheter assembly 416 suitable for use with the delivery device 10 of FIGS. 1A and 1B is the same as the catheter assembly 16 described above, except that the catheter assembly 416 includes a pull wire 400 affixed at a first end 401 to the transition piece 450, and extending through apertures 428a and 428b in the retainer 425 and through the lumen of the inner shaft 426 until terminating at a second end 402 coupled to the handle 20.

The pull wire 400 may be made of a stainless steel braided cable, for example. The first end 401 of the pull wire 400 is affixed to the transition piece 450 at or adjacent a distally-facing abutment surface 451 configured to abut against the proximal end of the distal sheath 24. The transition piece 450 further includes a proximal recess 452 extending into the proximal end thereof and configured to receive the distal end of the outer shaft 22.

The retainer 425 includes apertures 428a and 428b configured to slidably receive the pull wire 400 therethrough, such that the pull wire 400 may extend into the retainer through the aperture 428a and out of the retainer through the aperture 428b. An inner surface of the retainer 425 exposed between the apertures 428a and 428b may serve as a fulcrum or pulley over which the pull wire 400 may slide as it is pulled proximally, as described further below.

The inner shaft 426 includes an opening 429 extending from an outer surface of the inner shaft to a lumen within the inner shaft and sized to receive the pull wire 400 therethrough. It is preferable that the inner shaft 426 contain separate lumens therein for the pull wire 400 and a guide wire (not shown), although that need not be the case.

In one variation, the apertures 428a and 428b and the opening 429 may be replaced by a single opening that extends between an outside surface of the retainer 425 and a lumen within the inner shaft 426. In such an embodiment, an exposed surface within this single opening may serve as the fulcrum or pulley over which the pull wire 400 may slide as it is pulled proximally. In another variation, the apertures 428a and 428b may be replaced by a single aperture with a rib therein. In such an embodiment, an exposed surface of the rib within this single aperture may serve as the fulcrum or pulley over which the pull wire 400 may slide as it is pulled proximally.

The second end 402 of the pull wire 400 may be coupled to a spool assembly 460 affixed to the proximal end 12 of the handle 20. The spool assembly 460 may be configured to provide tension to the pull wire and to permit a user to provide a force to the second end of the pull wire in a proximal direction with mechanical advantage. The spool assembly 460 includes a fixed portion 470 that is affixed to the handle housing 30, and a rotatable portion 480 that is coupled to the fixed portion. The fixed portion 470 has a proximal nose portion 472 that is received in a corresponding recess 482 extending into a distal end of the rotatable portion 480.

The pull wire 400 extends through a central lumen 474 of the spool assembly 460 and out from the central lumen through an aperture 484 into a spooling compartment 486. The spooling compartment 486 surrounds a cylindrical spool 488 that is fixed to the rotatable portion 480. The second end 402 of the pull wire 400 is affixed to any location within the rotatable portion 480, for example, a location along the cylindrical spool 488. Alternatively, the cylindrical spool 488 may be fixed to the fixed portion 470, and in such an embodiment, the second end 402 of the pull wire 400 may be affixed to any location within the rotatable portion 480 except for the cylindrical spool.

The spool assembly 460 further includes a spring element (not shown) that is biased to rotate the rotatable portion 480 about the fixed portion 470 so that any additional length of the pull wire 400 automatically spools into the compartment 486 and about the spool 488 as the distal sheath is moved in a distal direction, thereby shortening the length of the pull wire that extends outside of the inner shaft 426.

In use of the catheter assembly 416 to deploy a valve into a patient, after loading a prosthetic valve into the compartment 23 and covering the valve with the distal sheath 24, the distal end 27 of the distal sheath initially abuts the proximally-facing abutment surface 15, and only a relatively short length of the pull wire 400 extends between the opening 429 and the distally-facing abutment surface 451 of the transition piece 450. The excess length of the pull wire 400 initially is wound around the spool 488 of the spool assembly 460.

As the user begins deployment of the valve by sliding the distal sheath 24 and the outer shaft 22 in a proximal direction to uncover the compartment 23, the transition piece 450 slides proximally with the outer shaft, thereby lengthening the portion of the pull wire 400 that extends between the opening 429 and the distally-facing abutment surface 451 of the transition piece, so additional pull wire length is withdrawn from the spool assembly 460 as the distal sheath is moved proximally.

If the user decides to resheath the valve by sliding the distal sheath 24 and the outer shaft 22 in a distal direction to cover the compartment 23, the transition piece 450 slides distally with the outer shaft, thereby shortening the portion of the pull wire 400 that extends between the opening 429 and the distally-facing abutment surface 451 of the transition piece. Consequently, as the distal sheath 24 slides distally, a portion of excess length of the pull wire 400 is re-wound around the spool 488 of the spool assembly 460.

Figure 5A:
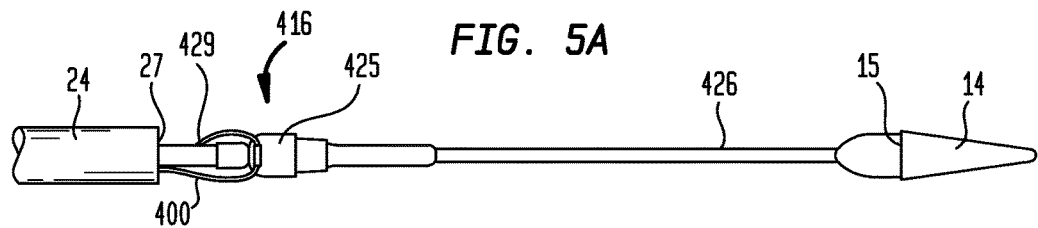
FIG. 5A is a side view of a portion of yet another catheter assembly suitable for use with the delivery device of FIG. 1A.
Figure 5B:
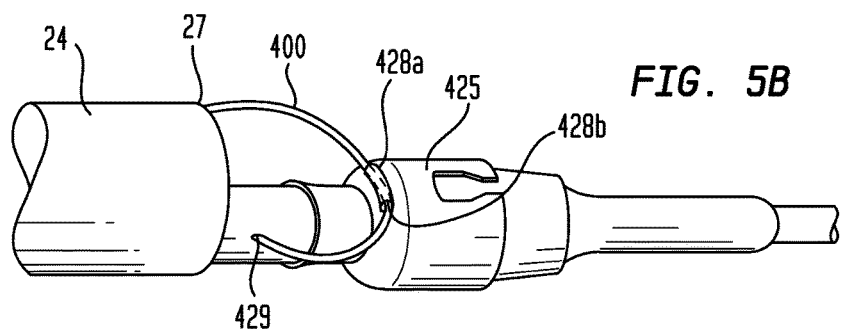
FIG. 5B is an enlarged perspective view of the retainer in the catheter assembly of FIG. 5A.
Figure 5C:
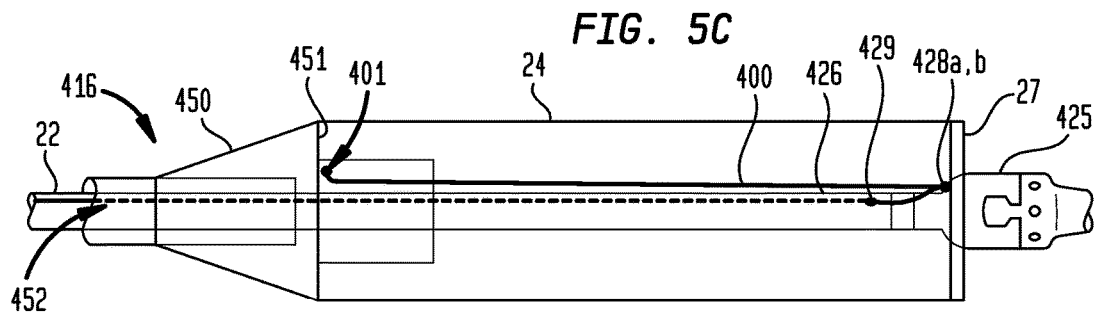
FIG. 5C is an enlarged schematic longitudinal cross-section illustrating the pull wire routing in the catheter assembly of FIG. 5A, with the distal sheath in a proximal position.
Figure 5D:
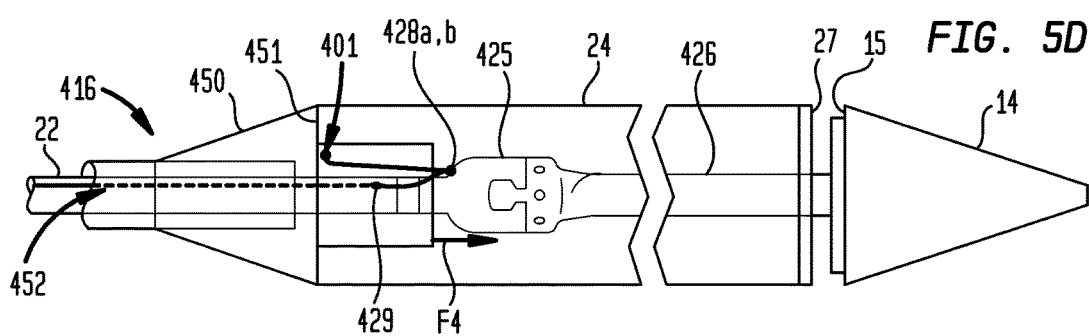
FIG. 5D is another enlarged schematic longitudinal cross-section illustrating the pull wire routing in the catheter assembly of FIG. 5A, with the distal sheath in a distal position.
Figure 5E:
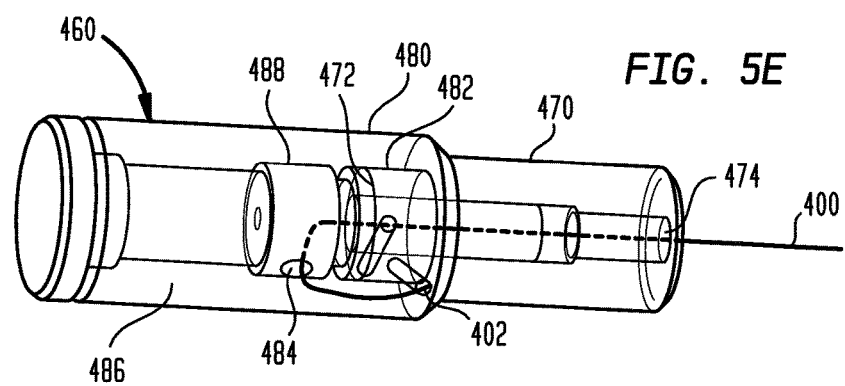
FIG. 5E is a perspective view of a pull wire spool assembly suitable for use with the catheter assembly of FIG. 5A.

Similar to the embodiment of FIG. 2A, after a valve contained within the compartment 23 of the catheter assembly 416 has been partially deployed and then resheathed as described above, the temporary axial compression of the outer shaft 22 may cause a gap to remain between the distal end 27 of the distal sheath 24 and the proximally-facing abutment surface 15 when the distal sheath is in its distal-most position, as can be seen in FIG. 5D (e.g., a gap of about 1 mm to about 15 mm), such that the distal sheath is in a partially closed condition covering a major portion of the compartment.

To axially stretch the outer shaft 22 to relieve the temporary axial compression thereof, the user may pull the second end 402 of the pull wire 400 proximally, either by rotating the rotatable portion 480 of the spool assembly 460 relative to the handle housing 30, or by grasping the second end of the pull wire and pulling proximally if a spool assembly is not used. The fulcrum or pulley of the apertures 428a and 428b in the retainer 425 serves to transfer the proximal force exerted by the user to a distal force F4 (FIG. 5D) that acts on the first end 401 of the pull wire 400 and the transition piece 450. Since the transition piece 450 is affixed to the distal end of the outer shaft 22, the force F4 acting on the transition piece will cause the transition piece to move in a distal direction toward the atraumatic tip 14, thereby axially stretching the outer shaft and closing the gap between the distal end 27 of the distal sheath 24 and the proximally-facing abutment surface 15.

Since the axial stretching of the outer shaft 22 will shorten the portion of the pull wire 400 that extends between the opening 429 and the distally-facing abutment surface 451 of the transition piece, as the outer shaft is stretched, a portion of excess length of the pull wire 400 is re-wound around the spool 488 of the spool assembly 460.

If the valve contained within the compartment 23 of the catheter assembly 416 is once again partially deployed and then resheathed during the same valve deployment procedure, thereby re-creating temporary axial compression of the outer shaft 22, the aforementioned process of axially stretching the outer shaft may be repeated to relieve such compression.

Although all of the embodiments herein have been described as relieving temporary compression of the outer shaft 22 after resheathing of a prosthetic heart valve, any of the devices and methods described herein may also be used to relieve temporary compression of the outer shaft after loading of a prosthetic heart valve into the compartment 23, to fully close the compartment before the catheter assembly is inserted into a patient. The outer shaft 22 may acquire temporary compression during loading of a prosthetic heart valve into the compartment 23 because the initial covering of the valve with the distal sheath may impart compressive forces onto the outer shaft.

Although all of the embodiments herein have been described as relieving temporary compression of the outer shaft 22 of a delivery device for inserting a prosthetic heart valve into a patient, any of the devices and methods described herein may also be used to relieve temporary compression of the outer shaft of a delivery device for any other type of medical device that can be delivered into a patient in a compartment that is covered by a distal sheath similar to those described herein. For example, a collapsible stent may be deployed into a patient using any of the devices described herein, and any of the devices and methods described herein may also be used to relieve temporary compression of the outer shaft of such a delivery device.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

In summary, the disclosure herein recites multiple embodiments to summarize the foregoing. Described herein is a delivery device for a collapsible prosthetic heart valve. The delivery device may include an operating handle having a housing and a carriage selectively fixed or movable relative to the housing, and a catheter assembly. The catheter assembly may include an inner shaft around which a compartment is defined, the inner shaft being operatively connected to the housing, the compartment being adapted to receive the valve in an assembled condition.

The catheter assembly may also include an outer shaft surrounding at least a portion of the inner shaft, the outer shaft being fixedly connected to the carriage and movable relative to the inner shaft and the housing, the outer shaft having a compressed length and an extended length greater than the compressed length along an axis of elongation of the outer shaft, a distal sheath fixedly connected to the outer shaft, the distal sheath being movable between a closed condition covering the compartment and an open condition uncovering the compartment for deployment of the valve, and a mechanism configured to apply a distal force to the outer shaft while the carriage is fixed relative to the housing to stretch the outer shaft from the compressed length to the extended length; and/or the mechanism may include a pressurized fluid source in communication with a lumen of the outer shaft and a fluid dam having a proximal-facing surface extending circumferentially around the inner shaft adjacent the compartment, the fluid dam being fixedly connected to the outer shaft and having an opening through which the inner shaft extends; and/or the fluid dam may be a portion of a transition piece that fixedly connects the outer shaft to the distal sheath; and/or the fluid dam may be a first fluid dam and the opening is a first opening, and the mechanism includes a second fluid dam having a proximal-facing surface located proximally of the first fluid dam and having a second opening through which the inner shaft extends, the second opening having a greater width than the first opening; and/or the inner shaft may include a recess configured to provide a region of extra fluid volume within the outer shaft at a location close to the fluid dam; and/or the mechanism may include a threaded portion of the inner shaft receivable inside an intermediate portion of a transition piece that fixedly connects the outer shaft to the distal sheath, the threaded portion and the intermediate portion each having threads that are configured to mate with one another; and/or the inner shaft may be longitudinally fixed relative to the housing, and the operating handle includes an actuator configured to rotate the inner shaft relative to the housing; and/or the catheter assembly may include a retainer coupled to the inner shaft within the compartment, the retainer including an inner piece and an outer piece mounted on the inner piece so as to be rotatable about the inner piece and constrained from movement relative to the inner piece along an axis of elongation of the inner shaft, the outer piece having a recess configured to receive a retention member of the valve; and/or the mechanism may include a pull wire having a first end fixedly coupled to the outer shaft and a second free end, and the inner shaft includes a fulcrum over which the pull wire extends, the fulcrum being located distally of the first end of the pull wire, the pull wire being configured such that when the second free end is pulled proximally, the distal force is applied to the outer shaft; and/or the inner shaft may include first and second lumens therein, and the pull wire extends within the first lumen between the operating handle and an opening adjacent the fulcrum; and/or the operating handle may further include a spooling assembly configured to automatically receive excess length of the pull wire as the distal sheath is moved distally.

Also described herein is another delivery device for a collapsible prosthetic heart valve. The delivery device may include an operating handle having a housing and a carriage selectively fixed or movable relative to the housing, and a catheter assembly. The catheter assembly may include an inner shaft around which a compartment is defined, the inner shaft being configured to be selectively coupled to and uncoupled from the housing, the compartment being adapted to receive the valve in an assembled condition.

The catheter assembly may also include an outer shaft surrounding at least a portion of the inner shaft, the outer shaft being fixedly connected to the carriage and movable relative to the inner shaft and the housing, the outer shaft having a compressed length and an extended length greater than the compressed length along an axis of elongation of the outer shaft, a distal sheath fixedly connected to the outer shaft, the distal sheath being movable between a closed condition covering the compartment and an open condition uncovering the compartment for deployment of the valve, and a mechanism configured to permit movement of the inner shaft relative to the outer shaft and the housing within a predetermined limit in distal and proximal directions; and/or the mechanism may include an energy storage element biased to move the inner shaft to a distalmost position when the inner shaft is uncoupled from the housing.

Also described herein is a method of fully enclosing a compartment of delivery device for implanting a medical device in a patient. The method may include providing the delivery device having a catheter assembly and an operating handle, the operating handle having a housing and a carriage selectively longitudinally fixed or movable relative to the housing, the catheter assembly including an inner shaft around which a medical device compartment is defined, an outer shaft surrounding at least a portion of the inner shaft, and a distal sheath fixedly connected to the outer shaft, the distal sheath being movable between a fully closed condition covering the compartment and an open condition uncovering the compartment.

The method may also include applying a distal force to the outer shaft while the carriage and the inner shaft are longitudinally fixed relative to the housing, thereby stretching the outer shaft from a compressed length to an extended length greater than the compressed length and moving the distal sheath to the fully closed condition, such that a distal end of the distal sheath contacts a proximally-facing abutment surface of the delivery device; and/or before the applying step, loading the medical device into the compartment of the catheter assembly and moving the distal sheath from the open condition to a partially closed condition covering a major portion of the compartment, such that the outer shaft is compressed from the extended length to the compressed length; and/or before the applying step, partially deploying the medical device by sliding the distal sheath to partially uncover the compartment and re-collapsing the medical device by sliding the distal sheath to a partially closed condition covering a major portion of the compartment, such that the outer shaft is compressed from the extended length to the compressed length; and/or before the partially deploying step, inserting the catheter assembly into the patient so that the medical device is positioned at a target location within the patient; and/or the applying step may include flowing a pressurized fluid within the outer shaft and against a proximal-facing surface of a fluid dam fixedly connected to the outer shaft; and/or the applying step may include decoupling the inner shaft from the housing and rotating the inner shaft relative to the outer shaft, thereby applying the distal force to a threaded transition piece fixedly connected to the outer shaft; and/or the catheter assembly may include a retainer coupled to the inner shaft and having a rotatable portion, the medical device has a retention member engaged within a recess of the retainer, and the medical device remains rotationally fixed relative to the distal sheath and relative to the rotatable portion of the retainer during the rotation of the inner shaft; and/or the catheter assembly may further include a pull wire having a first end fixedly coupled to the outer shaft and a second free end, and the inner shaft includes a fulcrum over which the pull wire extends, and the applying step includes pulling the pull wire in a proximal direction, thereby applying the distal force to the outer shaft; and/or the pull wire may be pulled in the proximal direction by rotating a portion of a spooling assembly coupled to the housing.

Also described herein is another method of fully enclosing a compartment of delivery device for implanting a medical device in a patient. The method may include providing the delivery device having a catheter assembly and an operating handle, the operating handle having a housing and a carriage selectively longitudinally fixed or movable relative to the housing, the catheter assembly including an inner shaft around which a medical device compartment is defined and configured to be selectively coupled to and uncoupled from the housing, an outer shaft surrounding at least a portion of the inner shaft, and a distal sheath fixedly connected to the outer shaft, the distal sheath being movable between a fully closed condition covering the compartment and an open condition uncovering the compartment.

The method may also include decoupling the inner shaft from the housing so that the inner shaft is movable relative to the housing, and pumping the inner shaft relative to the outer shaft and the housing while the carriage is fixed relative to the housing, thereby reducing compression of the outer shaft so that the outer shaft lengthens from a compressed length to extended length greater than the compressed length and moving the distal sheath to the fully closed condition, such that a distal end of the distal sheath contacts a proximally-facing abutment surface of the delivery device; and/or before the pumping step, loading the medical device into the compartment of the catheter assembly and moving the distal sheath from the open condition to a partially closed condition covering a major portion of the compartment, such that the outer shaft is compressed from the extended length to the compressed length; and/or before the applying step, partially deploying the medical device by sliding the distal sheath to partially uncover the compartment and re-collapsing the medical device by sliding the distal sheath to a partially closed condition covering a major portion of the compartment, such that the outer shaft is compressed from the extended length to the compressed length; and/or before the partially deploying step, inserting the catheter assembly into the patient so that the medical device is positioned at a target location within the patient; and/or the pumping step includes moving the inner shaft in a proximal direction, and the inner shaft is automatically returned to an initial distal position between successive proximal movements of the inner shaft by an energy storage element coupled between the housing and the inner shaft.

The invention claimed is:

1. A delivery device for a collapsible prosthetic heart valve, the delivery device comprising:
an operating handle having a housing and a carriage selectively fixed or movable relative to the housing; and
a catheter assembly, including:
an inner shaft around which a compartment is defined, the inner shaft being operatively connected to the housing, the compartment being adapted to receive the valve in an assembled condition;
an outer shaft surrounding at least a portion of the inner shaft, the outer shaft being fixedly connected to the carriage and movable relative to the inner shaft and the housing, the outer shaft having a compressed length and an extended length greater than the compressed length along an axis of elongation of the outer shaft;
a distal sheath fixedly connected to the outer shaft, the distal sheath being movable between a closed condition covering the compartment and an open condition uncovering the compartment for deployment of the valve; and
a mechanism configured to apply a distal force to the outer shaft while the carriage is fixed relative to the housing to stretch the outer shaft from the compressed length to the extended length.

2. The delivery device of claim 1, wherein the mechanism includes a pressurized fluid source in communication with a lumen of the outer shaft and a fluid dam having a proximal-facing surface extending circumferentially around the inner shaft adjacent the compartment, the fluid dam being fixedly connected to the outer shaft and having an opening through which the inner shaft extends.

3. The delivery device of claim 2, wherein the fluid dam is a portion of a transition piece that fixedly connects the outer shaft to the distal sheath.

4. The delivery device of claim 2, wherein the fluid dam is a first fluid dam and the opening is a first opening, and the mechanism includes a second fluid dam having a proximal-facing surface located proximally of the first fluid dam and having a second opening through which the inner shaft extends, the second opening having a greater width than the first opening.

5. The delivery device of claim 2, wherein the inner shaft includes a recess configured to provide a region of extra fluid volume within the outer shaft at a location close to the fluid dam.

6. The delivery device of claim 1, wherein the mechanism includes a threaded portion of the inner shaft receivable inside an intermediate portion of a transition piece that fixedly connects the outer shaft to the distal sheath, the threaded portion and the intermediate portion each having threads that are configured to mate with one another.

7. The delivery device of claim 6, wherein the inner shaft is longitudinally fixed relative to the housing, and the operating handle includes an actuator configured to rotate the inner shaft relative to the housing.

8. The delivery device of claim 6, wherein the catheter assembly includes a retainer coupled to the inner shaft within the compartment, the retainer including an inner piece and an outer piece mounted on the inner piece so as to be rotatable about the inner piece and constrained from movement relative to the inner piece along an axis of elongation of the inner shaft, the outer piece having a recess configured to receive a retention member of the valve.

9. The delivery device of claim 1, wherein the mechanism includes a pull wire having a first end fixedly coupled to the outer shaft and a second free end, and the inner shaft includes a fulcrum over which the pull wire extends, the fulcrum being located distally of the first end of the pull wire, the pull wire being configured such that when the second free end is pulled proximally, the distal force is applied to the outer shaft.

10. The delivery device of claim 9, wherein the inner shaft includes first and second lumens therein, and the pull wire extends within the first lumen between the operating handle and an opening adjacent the fulcrum.

11. The delivery device of claim 9, wherein the operating handle further includes a spooling assembly configured to automatically receive excess length of the pull wire as the distal sheath is moved distally.

12. A method of fully enclosing a compartment of delivery device for implanting a medical device in a patient, the method comprising:
providing the delivery device having a catheter assembly and an operating handle, the operating handle having a housing and a carriage selectively longitudinally fixed or movable relative to the housing, the catheter assembly including an inner shaft around which a medical device compartment is defined, an outer shaft surrounding at least a portion of the inner shaft, and a distal sheath fixedly connected to the outer shaft, the distal sheath being movable between a fully closed condition covering the compartment and an open condition uncovering the compartment; and
applying a distal force to the outer shaft while the carriage and the inner shaft are longitudinally fixed relative to the housing, thereby stretching the outer shaft from a compressed length to an extended length greater than the compressed length and moving the distal sheath to the fully closed condition, such that a distal end of the distal sheath contacts a proximally-facing abutment surface of the delivery device.

13. The method of claim 12, further comprising, before the applying step, loading the medical device into the compartment of the catheter assembly and moving the distal sheath from the open condition to a partially closed condition covering a major portion of the compartment, such that the outer shaft is compressed from the extended length to the compressed length.

14. The method of claim 12, further comprising, before the applying step, partially deploying the medical device by sliding the distal sheath to partially uncover the compartment and re-collapsing the medical device by sliding the distal sheath to a partially closed condition covering a major portion of the compartment, such that the outer shaft is compressed from the extended length to the compressed length.

15. The method of claim 14, further comprising, before the partially deploying step, inserting the catheter assembly into the patient so that the medical device is positioned at a target location within the patient.

16. The method of claim 12, wherein the applying step includes flowing a pressurized fluid within the outer shaft and against a proximal-facing surface of a fluid dam fixedly connected to the outer shaft.

17. The method of claim 12, wherein the applying step includes decoupling the inner shaft from the housing and rotating the inner shaft relative to the outer shaft, thereby applying the distal force to a threaded transition piece fixedly connected to the outer shaft.

18. The method of claim 17, wherein the catheter assembly includes a retainer coupled to the inner shaft and having a rotatable portion, the medical device has a retention member engaged within a recess of the retainer, and the medical device remains rotationally fixed relative to the distal sheath and relative to the rotatable portion of the retainer during the rotation of the inner shaft.

19. The method of claim 12, wherein the catheter assembly further includes a pull wire having a first end fixedly coupled to the outer shaft and a second free end, and the inner shaft includes a fulcrum over which the pull wire extends, and the applying step includes pulling the pull wire in a proximal direction, thereby applying the distal force to the outer shaft.

20. The method of claim 19, wherein the pull wire is pulled in the proximal direction by rotating a portion of a spooling assembly coupled to the housing.

* * * * *